(12) United States Patent
Qin et al.

(10) Patent No.: US 9,125,418 B2
(45) Date of Patent: Sep. 8, 2015

(54) AGRICULTURAL COMPOSITIONS

(75) Inventors: Kuide Qin, Westfield, IN (US); Lei Liu, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 901 days.

(21) Appl. No.: 12/369,123

(22) Filed: Feb. 11, 2009

(65) Prior Publication Data

US 2009/0202648 A1    Aug. 13, 2009

Related U.S. Application Data

(60) Provisional application No. 61/065,364, filed on Feb. 11, 2008.

(51) Int. Cl.
| | | |
|---|---|---|
| *A01N 59/16* | (2006.01) |
| *A01N 25/04* | (2006.01) |
| *A01N 25/30* | (2006.01) |
| *A01N 47/14* | (2006.01) |
| *A01N 25/22* | (2006.01) |

(52) U.S. Cl.
CPC ............... *A01N 59/16* (2013.01); *A01N 25/22* (2013.01)

(58) Field of Classification Search
CPC .............................. A01N 59/16; A01N 25/22
USPC ......................................................... 504/358
See application file for complete search history.

(56) References Cited

U.S. PATENT DOCUMENTS

| | | | | |
|---|---|---|---|---|
| 2,875,166 | A * | 2/1959 | Hopkins ..................... | 524/381 |
| 3,558,302 | A * | 1/1971 | Salvesen ..................... | 504/126 |
| 6,210,696 | B1 * | 4/2001 | Gore et al. ................... | 424/405 |
| 6,380,278 | B1 | 4/2002 | Fan et al. | |
| 6,399,672 | B1 | 6/2002 | Ceska et al. | |

FOREIGN PATENT DOCUMENTS

WO    WO00/75241 A2    12/2000

OTHER PUBLICATIONS

Smith, D., Unique Metal-Containing Acrylated Oligomers Impart Excellent Adhesion Characteristics, [online]. High Beam Research, Oct. 2004, [retrieved on Nov. 22, 2011]. Retrieved from the Internet: <URL:www.highbeam.com/doc/1G1-124641200.html>.pp. 1-6.*
Ceska, G.W., Leroy C., Schaeffer B.: "Hybrid Oligomers—Organic/Inorganic Acrylics" Sartomer, Oct. 2004.
Xinheng Yuan, et al. "In Situ Preparation of Zinc Salts of Unsaturated Carboxylic Acids to Reinforce NBR" Journal of Applied Polymer Science, John Wily and Sons Inc., New York, vol. 77, No. 12, Jul. 2000, pp. 2740-2748.
International Searching Authority, International Search Report for PCT/US2009/033739, dated Aug. 7, 2010, 4 pages.
International Searching Authority, Written Opinion for PCT/US2009/033739, dated Aug. 7, 2010, 5 pages.
International Searching Authority, International Preliminary Report on Patentability for PCT/US2009/033739, dated Aug. 17, 2010, 6 pages.
New Metal Containing Acrylated Oligomers Impart Excellent Adhesion in Coatings, dated Mar. 1, 2005, available online at http://www.pcimag.com/articles/new-metal-containing-acrylated-oligomers-impart-excellent-adhesion-incoatings.
"Unique Metal-Containing Acrylated Oligomers Impart Excellent Adhesion Characteristics," dated Oct. 1, 2004, Adhesives Magazine, 5 pages.
Zineb—Compound Summary, PubChem Public Chemical Database, available at http://pubchem.ncbi.nlm.nih.gov/summary/summary/cgi?cid=5284484, accessed Sep. 15, 2011, 4 pages.

* cited by examiner

*Primary Examiner* — John Pak
*Assistant Examiner* — Andriae M Holt
(74) *Attorney, Agent, or Firm* — C. W. Arnett; Faegre Baker Daniels LLP

(57) ABSTRACT

Compositions have been discovered that are suitable for forming a stable dispersion. The compositions comprise an agriculturally active compound and a multivalent metal oligomeric or polymeric compound having a molecular weight of from about 150 to about 15,000 Daltons.

9 Claims, 3 Drawing Sheets

*with 2.5% Nu-Film-17

AGRICULTURAL COMPOSITIONS

CROSS-REFERENCE TO RELATED APPLICATIONS

This application claims the benefit of U.S. Provisional Patent Application 61/065,364 filed on Feb. 11, 2008, which is expressly incorporated herein.

FIELD OF THE INVENTION

This invention relates to agricultural compositions comprising metallic oligomers or polymers.

BACKGROUND AND SUMMARY OF THE INVENTION

Oil-based agricultural compositions are often desirable in applications requiring, for example, a combination of properties such as penetration, spread, rainfastness, persistency, stability, compatibility, and the like. As described in U.S. Pat. No. 6,210,696, such oil based compositions may take the form of a dispersion. However, many such prior agricultural dispersions are limited in the types of agricultural compounds that may be employed and/or have limited efficacy, dispersion stability, rheology persistency, and compatibility. Thus, new formulations are needed that exhibit such desirable properties or combinations of properties.

Fortunately, the present invention provides water immiscible agricultural dispersions that often exhibit suitable or enhanced efficacy, dispersion stability, rheology persistency, and/or compatibility. The dispersions typically comprise a disperse phase comprising an agriculturally active compound; a continuous phase comprising a water immiscible liquid; and a metal compound having a molecular weight of from about 150 to about 15,000 Daltons. The agriculturally active compound may be selected from the group consisting of fungicides, insecticides, herbicides, nematocides, and mixtures thereof.

In another embodiment, the invention relates to compositions suitable for forming a dispersion. The compositions often comprise an agriculturally active compound selected from the group consisting of fungicides, insecticides, herbicides, nematocides, and mixtures thereof and a multivalent metal oligomeric or polymeric compound having a molecular weight of from about 150 to about 15,000 Daltons. Typically, the multivalent metal compound comprises two or more functional groups selected from the group consisting of acrylate, methacrylate, hydroxyl, carboxyl, ester and mixtures thereof.

In another embodiment, the invention relates to dispersions comprising from about 1 to about 70 weight percent based on the weight of the dispersion of ethylene bisdithiocarbamate, from about 0.001 to about 20 weight percent based on the weight of the dispersion of a multivalent metal compound, and an oil.

DETAILED DESCRIPTION OF THE INVENTION

General Definitions

Figure 1:
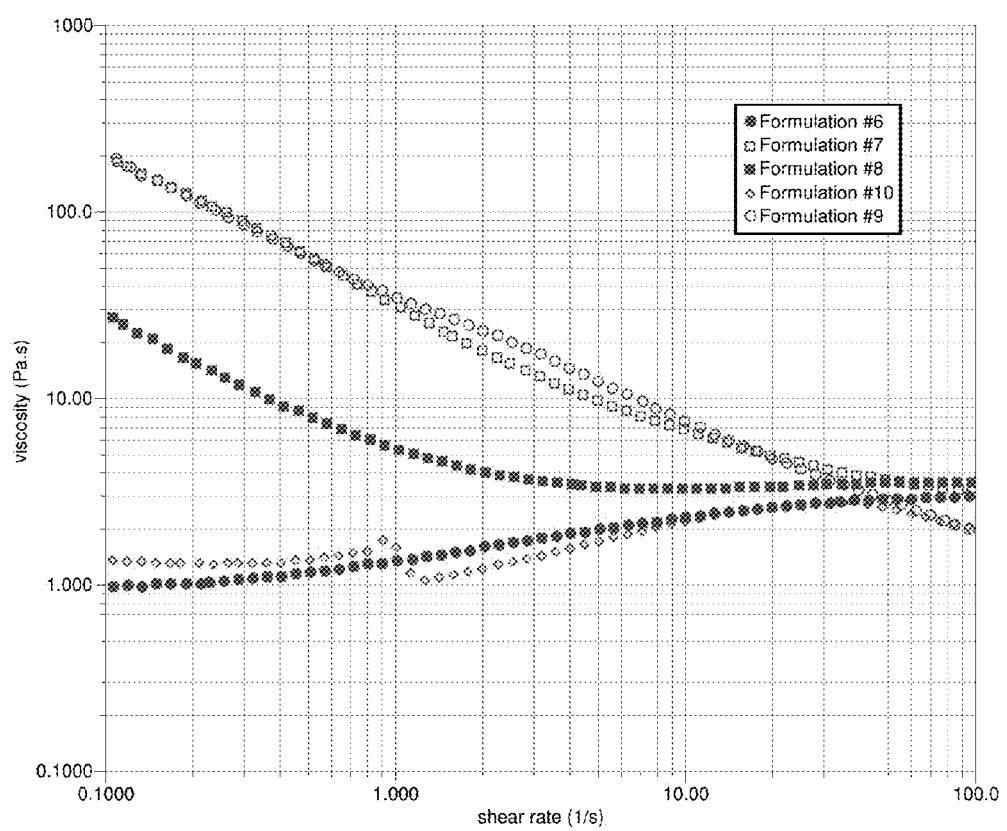
FIG. 1 is a plot showing viscosity (Pa·s) vs. shear rate (1/s) for the formulations of Examples 6-10.

"Polymer" means a polymeric compound prepared by polymerizing monomers, whether of the same or a different type. The generic term "polymer" embraces the terms "homopolymer," "copolymer," "terpolymer" as well as "interpolymer."

"Oligomer" means a polymer molecule comprising only a few monomer units such as a dimer, trimer, tetramer, etc.

"Composition," as used herein, includes a mixture of materials which comprise the composition, as well as reaction products and decomposition products formed from the ingredients or materials of the composition.

"Dispersion," as used herein, includes a mixture of materials which comprise the dispersion, as well as reaction products and decomposition products formed from the ingredients or materials of the dispersion.

"Agriculturally active compound" means any compound or mixture that is useful in increasing or maintaining the productivity or quality of an agricultural product.

Compositions

The present invention relates to compositions that may be suitable for dispersions. The compositions of the present invention typically comprise an agriculturally active compound and a metal compound which is typically an oligomeric or polymeric metal compound. Useful agriculturally active compounds typically include, for example, fungicides, insecticides, herbicides, nematocides, and mixtures thereof. The specific compound may vary depending upon, for example, form of the composition, the desired application, specific formulation, crop, and/or desired application rate. However, preferable compounds often include thiocarbamates, chlorinated nitrile, triazole, aralkyl triazole, triazole anilide, benzamide, alkyl benzamide, diphenyl ether, pyridine carboxylic acid, chloroaniline, organophosphate, phosphonic glycine salt, and agriculturally acceptable salts and mixtures thereof. A particularly preferable compound includes ethylene bisdithiocarbamate and agriculturally acceptable salts and mixtures thereof.

Useful agriculturally active compounds are typically solids at room temperature but may also include liquids. If the agriculturally active compound is to be employed in a dispersion then it is usually preferable that said agriculturally active compound be in a form that facilitates dispersability. Such forms may vary depending upon, for example, the application, the specific compound, the desired continuous phase, and/or other ingredients. However, a typical dispersible form includes a solid form at room temperature wherein the mean particle size is from about 0.01 to about 100 microns.

The solid form of the agriculturally active compound may include, for example, a particulate, a wettable powder, or dispersible granule. As one skilled in the art will appreciate the amount of active ingredient in such a particulate, a wettable powder, or dispersible granule will vary depending upon the solid form and the remainder of the particulate, wettable powder, or dispersible granule often comprises typical inactive ingredients such as carriers, dispersant, wetting agents, and/or surfactants. The solid form of the agriculturally active compound, e.g., a particulate, wettable powder, or dispersible granule, may also include the metal compound as described in detail below.

In addition to an agriculturally active compound the compositions of the present invention also include at least one metal compound which is typically an oligomeric or polymeric metal compound. Inclusion of such a metal compound has surprisingly and unexpectedly been found to sometimes provide enhanced disease control, dispersion stability, rheology persistency, or compatibility as compared to compositions lacking such a metal compound. In regard to the metal compound, useful compounds vary depending upon, for example, form of the composition, the agriculturally active compound, desired application, specific formulation, crop, and/or desired application rate. Typically, useful metal compounds often include at least one multivalent metal. The multivalent metal may be any suitable metal having a valency of two or more. Typically, the metal is selected from the group consisting of, for example, the metals of Groups IIA-IVA, IB-VIIB, group VIII transition metals. Preferable metals include, for example, zinc, aluminum, magnesium, calcium, copper, iron, manganese, or mixtures thereof.

The molecular weight of the metal compound may vary also depending upon, for example, the form of the composition, the agriculturally active compound, desired application, specific formulation, crop, and/or desired application rate. For many applications it has been found that metal compounds having a molecular weight of at least about 150, more preferably at least about 300. On the other hand, metal compounds having a molecular weight of at most about 15,000, more preferably at most about 5000 may be particularly effective.

Typically, the metal compound comprises a polymeric or oligomeric components. The polymeric or oligomeric components often comprises two or more functional groups. Preferable polymeric or oligomeric components include those selected from a urethane, a polyester, and mixtures thereof. Preferable functional groups include, for example, those selected from the group consisting of acrylate, methacrylate, hydroxyl, carboxyl, ester, and mixtures thereof. Suitable metal compounds are described in, for example, "Hybrid Oligomers-Organic/Inorganic Acrylics" by G. Ceska, C. Leroy, and W. Schaeffer of Sartomer Co. and in U.S. Pat. Nos. 6,380,278 and 6,399,672, all of which are incorporated herein by reference. Preferable metal compounds include metallic acrylate esters such as zinc acrylate esters, metallic acrylate oligomers such as zinc acrylate oligomers, and mixtures thereof.

While not wishing to be bound by any theory it is believed that when the composition is in the form of a dispersion the metal compound facilitates enhanced dispersion stability by having the metal portion anchored to the surface of the agriculturally active compound particles while the polymeric or oligomeric portion extends into the continuous phase. This facilitates the formation of steric barriers and promotes the dispersion's stability.

The metal compound may take any form. That is, it may be in solid or liquid admixture with the agriculturally active compound. The ratio of agriculturally active compound to metal compound varies depending upon the ingredients, the desired form and the application. Typically, the weight ratio of active compound to metal compound is from about 0.1 to about 10,000, preferably from about 1 to 100.

The compositions comprising an agriculturally active compound and a metal compound may also comprise suitable additives. Suitable additives may include, for example, surfactants, dispersants, emulsifiers, buffers, thickeners, etc.

Dispersions

As described above, the compositions of the present invention may be formulated into dispersions. Such dispersions typically comprise a disperse phase and continuous phase. The disperse phase typically comprises the agriculturally active compound while the continuous phase typically comprises a water immiscible liquid. Suitable water immiscible liquids may be selected based upon the agriculturally active compound and the desired properties. Suitable water immiscible liquids often include, for example, an oil such as paraffinic oil, as well as petroleum distillates, glycerides, vegetable oils, esters of vegetable oils, and mixtures thereof.

The amounts of agriculturally active compound, metal compound, surfactant (if present), and water immiscible liquid vary depending upon the specific ingredients and desired application of the dispersion. Typically, the amount of agriculturally active compound is from about 0.1 to about 70, preferably from about 1 to about 60 weight percent based on the total weight of the dispersion. Typically, the amount of metal compound is from about 0.01 to about 20, preferably from about 0.1 to about 5 weight percent based on the total weight of the dispersion. Typically, the amount of water immiscible liquid is from about 10 to about 99, preferably from about 30 to about 95 weight percent based on the total weight of the dispersion. Typically, if present, the amount of surfactant is from about 0.01 to about 30, preferably from about 0.1 to about 10 weight percent based on the total weight of the dispersion.

A particularly effective dispersion comprises from about 30 to about 60 weight percent based on the weight of the dispersion of ethylene bisdithiocarbamate, from about 0.1 to about 5 weight percent based on the weight of the dispersion of a multivalent metal compound selected from zinc acrylate oligomer and zinc acrylate ester, and an oil. Said dispersion preferably further comprises from about 0.1 to about 10 weight percent based on the weight of the dispersion of a non-ionic surfactant selected from the group consisting a block copolymer of ethylene oxide, a block copolymer of propylene oxide, block copolymers of ethylene oxide and propylene oxide, and mixtures thereof.

The aforementioned dispersions may be formed in any convenient manner. The properties of the dispersion are usually unaffected by the order of addition of ingredients so long as the ingredients are mixed properly. For convenience, typically the inert ingredients are first dissolved into the water immiscible liquid. The agriculturally active compound is then mixed in until it is dispersed. The oligomeric or polymeric metal compound is then added and mixed to form the final dispersion.

The dispersions of this invention are typically applied in the field as dilutions into oil or water or oil/water/surfactant carriers. Such dilutions may be in the range of 1-2000 fold depending on the market and the applications. The spray tank mixtures may contain other formulated agronomic compositions such as, for example, adjuvants, insecticides, miticides, fertilizers, pesticides, herbicides, nematocides, and mixtures thereof. Application onto suitable crops may be made by ground or aerial spray equipment.

The dispersions of the present invention often exhibit good properties or combination of properties. Such properties include, for example, good rheological properties such as control of shear viscosity over a wide shear rate range and suitable yield point at relatively low concentrations. The dispersions are usually physically stable under high and low temperatures and have low amounts of phase separation while at the same time providing enhanced efficacy and disease control. The dispersions show rainfastness and persistent efficacy under normal rain conditions, and beneficially may provide even additional rainfastness when exposed to ultraviolet light. The dispersions also exhibit compatibility with other compounds with little or no flocculation, and visual suspensability. In some cases, a synergistic thickening effect is observed in composition comprising (1) block copolymers selected from the group consisting of ethylene oxide, propylene oxide, and mixtures thereof such as the Pluronic™ and Tectronic™ series of products available from BASF, the specification sheets of which are incorporated herein by reference and (2) metal compounds selected from the group consisting of zinc acrylate oligomers and/or zinc acrylate esters such as the CN 2400™ series of products available from Sartomer Company, Inc., the specification sheets of which are incorporated herein by reference.

Examples 1-3

Three formulations were made by mixing 0.5% by weight oleic acid, 1% by weight of a dispersant which is polyisobutylene succinic anhydride-polyethylene glycol (Atlox 4914™ available from Croda, Inc. of which the specification sheet is incorporated herein by reference), 0.3% by weight of a non-ionic surfactant which is a tetrafunctional block copolymer terminating in primary hydroxyl groups (Tetronic 304™ having an HLB 12-18 available from BASF of which the specification sheet is incorporated herein by reference), 5% by weight of a non-ionic surfactant which is a secondary alcohol ethoxylate (Tergitol 15-S-5™ having an HLB 10.5 available from The Dow Chemical Company of which the specification sheet is incorporated herein by reference), 47.1% by weight of an agriculturally active compound which is Mancozeb, and an amount of metal compound, i.e., zinc acrylate oligomer (CN2404™ available from Sartomer Company, Inc.) or zinc acrylate ester (CN 2401™ available from Sartomer Company, Inc.), as shown in Table 1 below. A water immiscible liquid which is an agricultural oil Prorex36™ available from ExxonMobil, comprised the balance of the formulation. Bioefficacy as to downy mildew (PLASVI) on grapes was tested by spraying each formulation at a spray rate of 104 ppm onto the grapes. The disease control was evaluated two weeks after the inoculation. The formulations containing the metal compound exhibited enhanced disease control as shown in Table 1.

TABLE 1

| Example | CN2404 ™ % w/w | CN2401 ™ % w/w | % disease control |
|---------|----------------|----------------|-------------------|
| 1       | 0.675          | 0              | 80                |
| 2       | 0              | 2              | 67                |
| 3[1]    | 0              | 0              | 60                |

[1]Comparative example

Examples 4-8

[1] Formulations 5, 6, and 7 were made by mixing 0.5% by weight oleic acid, 1% by weight of a dispersant which is polyisobutylene succinic anhydride-polyethylene glycol (Atlox 4914™ available from Croda, Inc. of which the specification sheet is incorporated herein by reference), 0.3% by weight of a non-ionic surfactant which is a tetrafunctional block copolymer terminating in primary hydroxyl groups (Tetronic 304™ having an HLB 12-18 available from BASF of which the specification sheet is incorporated herein by reference), 5% by weight of a non-ionic surfactant which is a secondary alcohol ethoxylate (Tergitol 15-S-5™ having an HLB 10.5 available from The Dow Chemical Company of which the specification sheet is incorporated herein by reference), 47.1% by weight of an agriculturally active compound which is Mancozeb, and an amount of metal compound, i.e., zinc acrylate oligomer (CN2404™ available from Sartomer Company, Inc.) or zinc acrylate ester (CN 2401™ or CN 2402™ available from Sartomer Company, Inc.), as shown in Table 2 below. A water immiscible liquid which is an agricultural oil Prorex 36™ available from ExxonMobil, comprised the balance of the formulation.

[2] As Table 2 below shows, Formulations 4 and 8 were comparative examples made in a similar manner to Formulations 5, 6, and 7 except that Formulation 4 was made without a metal compound while Formulation 8 was made without a metal compound and without the 0.3% by weight of the Tetronic 304™ used in Formulations 5-7.

[3] Formulations 4-8 were tested for thickening effect, by using a rheometer AR1000 from TA Instruments and a cone and plate setup in the shear rate range of 0.1 1/s-100 1/s. The results of FIG. 1 show that Formulations 5-7 are able to effectively build up the low shear viscosity and to keep or even lower the high shear viscosity. FIG. 1 also showed the effect of zinc acrylates as oil thickening agents. All the zinc acrylates were able to build up the low shear viscosity yet to keep or even lower the high shear viscosity, which is highly desirable for high solid loading suspensions. The measurements were done with a rheometer AR1000 from TA Instruments using a cone and plate setup in the shear rate range of 0.1 1/s-100 1/s. The corresponding formulation compositions were shown in Table 2.

TABLE 2

| Example | CN2404 ™ % w/w | CN2401 ™ % w/w | CN2402 ™ % w/w |
|---------|----------------|----------------|----------------|
| 4[1]    | 0              | 0              | 0              |
| 5       | 0              | 2              | 0              |
| 6       | 0              | 0              | 2              |
| 7       | 2              | 0              | 0              |
| 8[2]    | 0              | 0              | 0              |

[1]Comparative example without a metal compound
[2]Comparative example without a metal compound and without the Tetronic non-ionic surfactant Examples 9-10

[4] Formulation 9 was a comparative example made in a similar manner to Formulation 4 except that 0.6% by weight of a non-ionic surfactant which is a tetrafunctional block copolyer terminating in primary hydroxyl groups (Tetronic 304™ having an HLB 12-18 available from BASF of which the specification sheet is incorporated herein by reference) was employed instead of 0.3% by weight of that surfactant that was used in Formulation 4.

[5] Formulation 10 was made in a similar manner to Formulation 7 except that 1% by weight of a metal compound, i.e., zinc acrylate oligomer (CN2404™ available from Sartomer Company, Inc.) was employed instead of 2% by weight of that metal compound that was used in Formulation 7.

Figure 2:
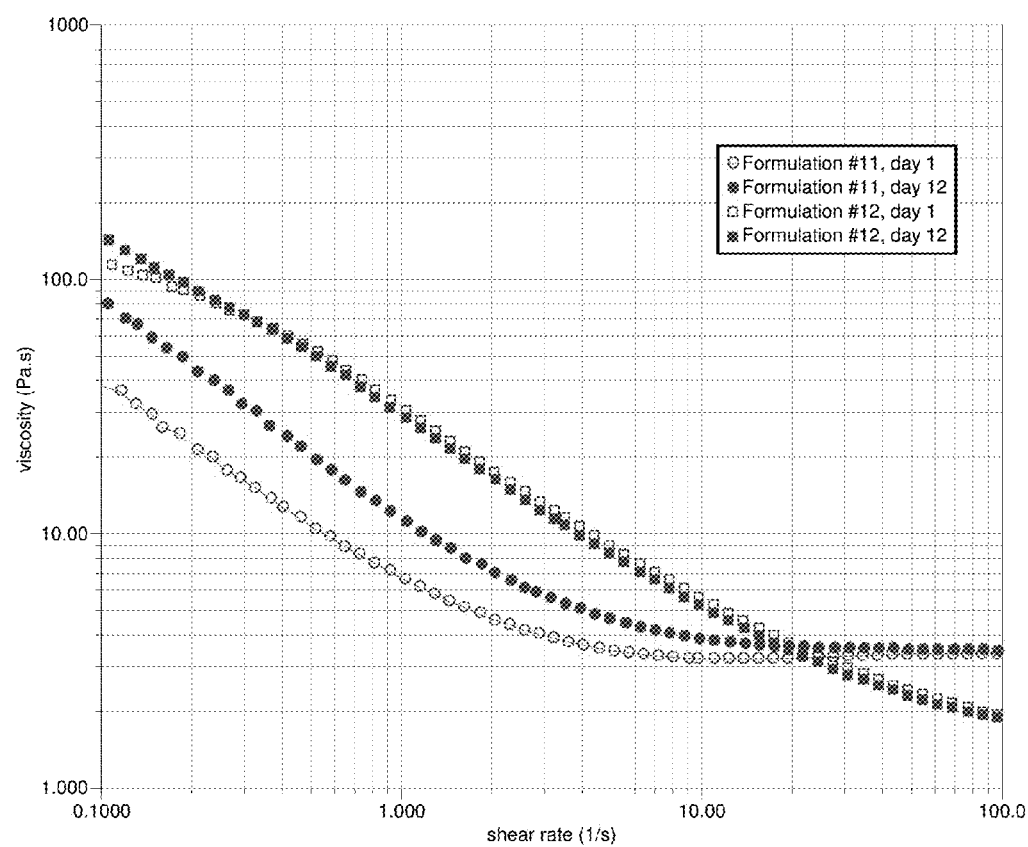
FIG. 2 is a plot showing viscosity (Pa·s) vs. shear rate (1/s) for the formulations of Examples 9-10 on the first day the formulations were made and 12 days after the formulations were made.

[6] The initial thickening effect was tested on Formulations 9 and 10 on the day they were made by using a rheometer AR1000 from TA Instruments and a cone and plate setup in the shear rate range of 0.1 1/s-100 1/s. Using the same method, Formulations 9 and 10 were tested again for thickening effect on the twelfth day after they were made. The results shown in FIG. 2 show that Formulation 10 containing the metal compound was more Theologically persistent, i.e., stable over time, than Formulation 9 which exhibited a significant viscosity drop over time, especially for the low shear viscosity. Specifically, the results show a significant viscosity drop, especially in the low shear region, was observed on formulation 9 without zinc acrylate additives, while the viscosity of formulation 10 containing zinc acrylate was stabilized over the measured shear rate range. The measurements were done using the same method as in FIG. 1.

Examples 11-14

[7] Four formulations were made by mixing 0.5% by weight oleic acid, 1% by weight of a dispersant which is polyisobutylene succinic anhydride-polyethylene glycol (Atlox 4914™ available from Croda, Inc. of which the specification sheet is incorporated herein by reference), 7% by weight of a non-ionic surfactant which is a secondary alcohol ethoxylate (Tergitol 15-S-5™ having an HLB 10.5 available from The Dow Chemical Company of which the specification sheet is incorporated herein by reference), 36.78% by weight of an agriculturally active compound which is Mancozeb, and the type and amount of additives shown in Table 3 below. A water immiscible liquid which is an agricultural oil Prorex 36™ available from ExxonMobil, comprised the balance of the formulation.

TABLE 3

| Example | Additive % w/w |
|---|---|
| 11 | 1.4% Atlox[2] LP6 ™ |
|  | 3% Tetronic 304 |
|  | 2% CN2404 |
| 12 | 1.4% Atlox LP6 ™ |
|  | 0.7% Tetronic 304 |
|  | 4% CN2404 |
| 13[1] | 1.4% Atlox LP6 ™ |
|  | 3% Tetronic 304 |
| 14[1] | 1.4% Atlox LP6 ™ |

[1]Comparative example
[2]Tetronic 304 ™ and CN2404 ™ are as described above. Atlox LP6 ™ (poly(12-hydroxyoctadecanoic acid-co-ethylenimine) and is described on its specification sheet as a polymeric dispersant in high boiling petroleum fraction which is available from Croda, Inc. of which the specification sheet is incorporated herein by reference.

[8] To test for compatibility 12% by weight of each of the Formulations 11-14 was mixed with 86% by weight paraffinic oil (Banole oil) and 2% by weight Triazole EC (Baycor DC300) for form Examples 11A-14A. Each of the four resulting formulations 11A-14A was observed for flocculation, settling, and suspensibility. The results shown in Table 4 indicate that the formulations containing a metal compound exhibited excellent compatibility with other compounds, i.e., stability.

TABLE 4

| Mixing Compatibility with Triazole EC | | | |
|---|---|---|---|
| Example | Flocculation | Settling over 24 hours | Visual suspensibility |
| 11A | No | No | Excellent |
| 12A | No | No | Excellent |
| 13A | Little | Some | Good |
| 14A | Yes | Yes | Poor |

Example 15

Figure 3:
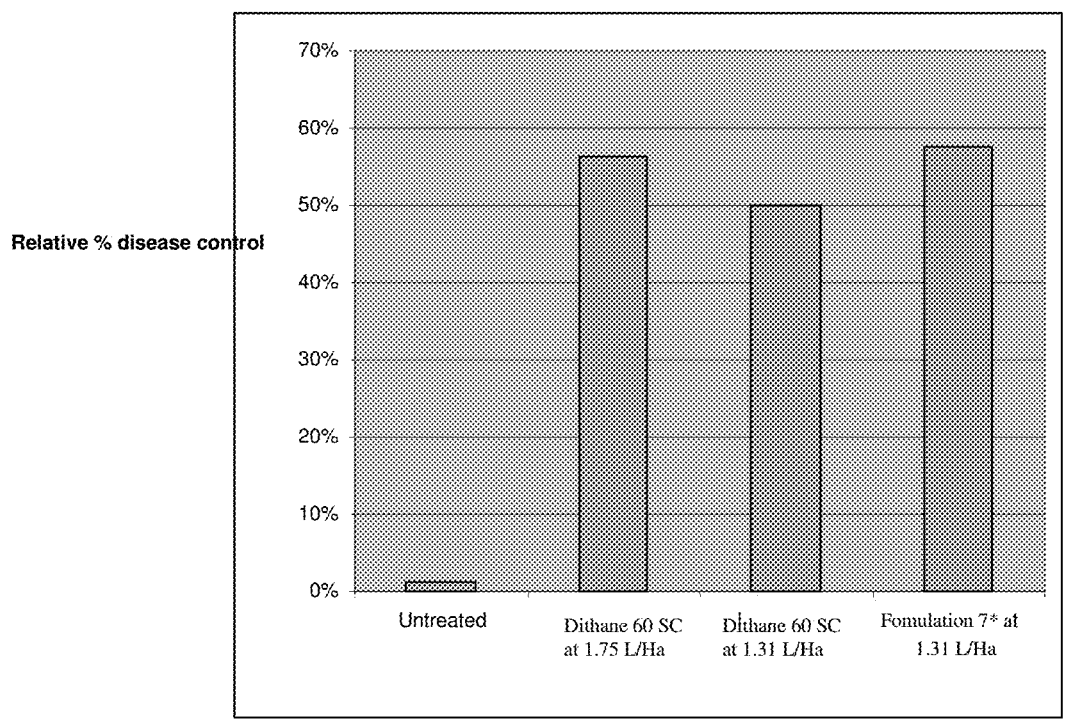
FIG. 3 is a graph showing the results of Example 15 comparing the relative percentage of disease control of formulation 7 vs. Dithane 60 SC™ on banana trees.

[9] A field trial was performed on banana trees to compare the performance of formulation 7 above against Dithane 60 SC™. First, 2.5% of Nu-Film-17 extender was added to formulation 7. The resulting formulation was applied to a group of banana trees weekly at a rate of 1.31 L/Ha for 12 consecutive weeks. Dithane 60 SC™ was applied to a second group of banana trees at a rate of 1.31 L/Ha for the same consecutive 12 weeks. Dithane 60 SC™ was applied to a third group of banana trees at a rate of 1.75 L/Ha for the same consecutive 12 weeks. A fourth group of banana trees were left untreated as a control for the same consecutive 12 weeks. FIG. 3 shows the results of accumulated assessment among all 12 applications. It can be seen the inventive formulation showed improved disease control even at a 25% less application rate than the Dithane 60 SC™.

[10] While the invention has been described with respect to a limited number of embodiments, the specific features of one embodiment should not be attributed to other embodiments of the invention. No single embodiment is representative of all aspects of the invention. In some embodiments, the compositions or methods may include numerous compounds or steps not mentioned herein. In other embodiments, the compositions or methods do not include, or are substantially free of, any compounds or steps not enumerated herein. Variations and modifications from the described embodiments exist. Finally, any number disclosed herein should be construed to mean approximate, regardless of whether the word "about" or "approximately" is used in describing the number. The appended embodiments and claims intend to cover all those modifications and variations as falling within the scope of the invention.

The invention claimed is:

1. A dispersion comprising:
    a disperse phase including an agriculturally active compound, wherein the agriculturally active compound comprises 30 wt. % to 60 wt. % of the total weight of the dispersion, and wherein the agriculturally active compound is ethylene bisdithiocarbamate and agriculturally acceptable salts and mixtures thereof;
    a continuous phase comprising a water immiscible liquid; and
    from about 0.675 wt. % to about 2.0 wt. % of a metal compound having a molecular weight of from about 500 to about 15,000 Daltons, wherein the metal compound is selected from the group consisting of a zinc acrylate esters and a zinc acrylate oligomer.

2. The dispersion of claim 1 wherein the water immiscible liquid is an oil.

3. The dispersion of claim 1 wherein the water immiscible liquid is selected from the group consisting of petroleum distillates, glycerides, vegetable oils, esters of vegetable oils, and mixtures thereof.

4. The dispersion of claim 1, further comprising a non-ionic surfactant.

5. The dispersion of claim 4, wherein the non-ionic surfactant is selected from the group consisting of: a block copolymer of ethylene oxide, a block copolymer of propylene oxide, block copolymers of ethylene oxide and propylene oxide, and mixtures thereof.

6. The dispersion of claim 4, wherein the dispersion comprises from about 0.1 wt. % to about 10 wt. % of a non-ionic surfactant based on the weight of the dispersion.

7. The dispersion of claim 1 wherein the agriculturally active compound is characterized by particles having a mean particle size of from about 0.01 to about 100 microns.

8. A dispersion, comprising:
    about 30 wt. % to about 60 wt. % ethylene bisdithiocarbamate;
    about 0.675 wt. % to about 2.0 wt. % multivalent metal compound selected from the group consisting of: zinc acrylate oligomer and zinc acrylate ester; and
    an oil.

9. The dispersion of claim 8, further comprising about 0.1 wt. % to about 10 wt. % of a non-ionic surfactant selected from the group consisting of: a block copolymer of ethylene oxide, a block copolymer of propylene oxide, block copolymers of ethylene oxide and propylene oxide.

* * * * *